(12) United States Patent
Paufique

(10) Patent No.: US 8,137,707 B2
(45) Date of Patent: Mar. 20, 2012

(54) METHOD OF OBTAINING AN ACTIVE INGREDIENT INCREASING CUTANEOUS CELL AND TISSUE LONGEVITY, ACTIVE INGREDIENTS AND COMPOSITIONS

(75) Inventor: Jean Paufique, Objat (FR)

(73) Assignee: Societe Industrielle Limousine d'Application Biologique, Dite Silab, Objat (FR)

( * ) Notice: Subject to any disclaimer, the term of this patent is extended or adjusted under 35 U.S.C. 154(b) by 108 days.

(21) Appl. No.: 12/373,215

(22) PCT Filed: Jul. 6, 2007

(86) PCT No.: PCT/FR2007/051610
§ 371 (c)(1),
(2), (4) Date: Jan. 9, 2009

(87) PCT Pub. No.: WO2008/007004
PCT Pub. Date: Jan. 17, 2008

(65) Prior Publication Data
US 2010/0009018 A1 Jan. 14, 2010

(30) Foreign Application Priority Data
Jul. 11, 2006 (FR) .................................... 06 52900

(51) Int. Cl.
*A61K 36/00* (2006.01)

(52) U.S. Cl. ....................................................... 424/725

(58) Field of Classification Search .................. None
See application file for complete search history.

(56) References Cited

U.S. PATENT DOCUMENTS

| 2004/0052758 A1 | 3/2004 | Paufique |
| 2005/0153003 A1 | 7/2005 | Menon et al. |
| 2007/0134189 A1 | 6/2007 | Golz-Berner et al. |

FOREIGN PATENT DOCUMENTS

| DE | 10 2004 007 385 | | 9/2005 |
| FR | 2 465 484 | | 3/1981 |
| FR | 2465484 | * | 3/1981 |
| FR | 2 669 032 | | 5/1992 |
| FR | 2669032 | * | 5/1992 |
| FR | 2735026 | * | 6/1995 |
| FR | 2 735 026 | | 12/1996 |
| FR | 2 741 265 | | 5/1997 |
| FR | 2741265 | * | 5/1997 |
| FR | 2 802 418 | | 6/2001 |
| FR | 2 814 676 | | 4/2002 |

OTHER PUBLICATIONS

Hayder et al. Anti-Genotoxic and Free-Radical Scavenging Activities of Extracts From (Tunisian) Myrtus Communis. Mutation Research. 564. (2004). pp. 89-95.*

Dermatology; Syneron Launches New Matrix IR Fractional Treatment Applicator for Wrinkle Treatment. Obesity, Fitness & Wellness Week, Atlanta, GA; Jun. 9, 2007, p. 466, pp. 1-2 of ProQuest.*

Philipson. New Drugs From Nature—It Could Be Yew. Phytotherapy Research. 13. 1999. pp. 2-8.*

Revilla et al. Comparison of Several Procedures Used for the Extraction of Anythocyanins From Red Grapes. J. Agric. Food Chem. 46. 1998. pp. 4592-4597.*

* cited by examiner

*Primary Examiner* — Melenie McCormick
(74) *Attorney, Agent, or Firm* — Oblon, Spivak, McClelland, Maier & Neustadt, L.L.P.

(57) ABSTRACT

Method for obtaining of an active principle from *Myrtus communis* in order to increase the longevity of the cells and tissues of the skin.

8 Claims, No Drawings

METHOD OF OBTAINING AN ACTIVE INGREDIENT INCREASING CUTANEOUS CELL AND TISSUE LONGEVITY, ACTIVE INGREDIENTS AND COMPOSITIONS

This invention relates to a method for obtaining of an active principle deriving from *Myrtus communis*, in order to increase cellular and tissue longevity and limit the occurrence of the signs of cutaneous aging.

The invention also relates to the active principle able to be obtained by this method and the associated cosmetic compositions.

With the increase in life expectancy, more and more importance is given to the aging of the skin.

Women and men tend to want to remain young for as long a time as possible and seek to delay and limit the appearance of indications of cutaneous aging, the first outward signs of aging.

Aging is a complex process dependent upon genetic determinism, epigenetic mechanisms, and various external influences such as sun, atmospheric pollution, diet, healthful living, etc. The longevity and the decline of the cells and tissues of the skin therefore are under the influence of numerous factors.

In order to prevent cutaneous aging effectively and to limit the appearance of the harmful effects ensuing therefrom, it is important to delay the phenomena of cellular senescence and to limit tissue degeneration.

That is why this invention proposes a method for obtaining of an active principle deriving from *Myrtus communis*, capable of limiting and reversing the appearance of signs of cutaneous aging by acting on at least three molecular mechanisms highly involved in cellular and tissue longevity.

In man, aging is associated with an increase in the percentage of body fat. It recently has been demonstrated that the activation of SIRT-1 proteins reduces the accumulation of fats in the adipose tissues by suppressing a transcription factor participating in adipogenesis. By simulating a caloric restriction, SIRT-1 brings about beneficial effects at the longevity level.

The SIRT-1s also play a part in various biological functions such as transcription, DNA repair, the processes of apoptosis and cellular senescence. These are key regulators of cellular survival.

Now, the endogenous expression of the SIRT-1s decreases progressively in aging human fibroblasts.

In fact, this invention has as its objective to promote the expression of the SIRT-1 longevity genes and thus reduce the phenomena of cellular senescence and increase the longevity of the cells and tissues of the skin.

Epigenetic factors also are involved in the explanation of the decline of functions in the course of aging.

That is the case, in particular, of the communication among the cells which is essential to their proper functioning and therefore guaranteeing their longevity. As a matter of fact, it is involved in numerous biological mechanisms such as assimilation of nutriments, apoptosis, transmission of information, etc.

All communication among cells and tissues takes place via receptors that recognize a messenger and transmit a message to the interior of the cell. A major aspect of membranous transmission is the need to assemble rapidly and effectively all the components involved in the transduction of the signal. This assembly is possible by virtue of the presence of specialized membranous micro-domains, such as the caveolae, that ensure contact between the receptor and its activation pathways. The caveolae are specialized lipid-enriched structures characterized by the presence of proteins referred to as caveolins. The caveolins interact directly with the signaling molecules such as the EGF (Epidermal Growth Factor) receptor, the G protein, the C kinase protein, etc.

Senescent cells are characterized by the deterioration of their membrane bringing about a dysfunction of the membranous signaling equipment. These senescent cells no longer react to the EGF-type growth factors, which leads to the loss of their proliferative capacity. This limited response of the senescent cells to intrinsic or extrinsic stress is due to an increase in the percentage of caveolin in the caveolae which causes a dysfunction of endocytosis.

The state of senescence of the cells can be reversed to an active functional state by restoring the membranous signaling equipment. In particular, by limiting the formation of caveole structures, it is possible to restore the signaling pathways regulated by the EGF in the senescent cells and re-stimulate their proliferative capacities.

Likewise, this invention therefore also proposes to reduce the expression of the caveolins in the membranes of the skin cells and in this way to stimulate cellular signaling and limit cellular senescence.

One of the characteristics of aging is the slowing down of cellular functioning possibly leading to the production of molecules that are changed and therefore incapable of performing their tasks normally.

Among these changes, glycation is known to be one of the principal causes of skin aging.

Glycation is the series of reactions that occur in the absence of enzymes between reducing sugars, such as glucose, and the protein free amino groups. It brings about the formation of abnormal and irreversible cross-bonds between the matrix macromolecules via the formation of glycation residues. In this way it changes the properties of the macromolecules making up the extracellular matrix, in particular of the collagens. The glycated proteins lose their biological functionality: the cutaneous tissues become rigid and sclerosed and tissue aging is accelerated.

That is why this invention also seeks to block the glycation reaction of the proteins involved in accelerated aging, so as to preserve the functionality of the cutaneous tissues and to increase the tissue longevity of the skin.

The active principle according to this invention therefore makes it possible to delay the phenomena of cellular senescence of the skin and to limit tissue degeneration by acting at once on genetic and epigenetic factors, namely:
- by stimulating the expression of the caloric restriction gene SIRT-1,
- by controlling intercellular signaling, in particular by reducing the expression of caveolin-1, an
- by limiting the glycation phenomenon, in particular collagen glycation.

In this way, by stimulating the molecular mechanisms highly involved in cellular and tissue longevity, the active principle according to the invention makes it possible to preserve the functionality of the skin tissues. It limits the degeneration of the cutaneous tissues and the appearance of signs of aging in the skin.

This invention now is described in detail in order to make it possible to better understand the obtained results compiled in tables.

I/ Method for Obtaining of the Active Principle According to the Invention

The method for obtaining of the active principle according to this invention comprises the sequence of the following steps:

solubilization of *Myrtus communis* powder in water in acid medium, preferentially of powder of *Myrtus communis* leaves, simultaneous and/or successive enzymatic hydrolysis/hydrolyses, separation of the soluble and insoluble phases by filtration, centrifugation or decantation, inactivation by thermal treatment, purification by clarification, concentration of the active fraction, filtration, and sterilizing filtration.

II/ Characterization of the Active Principle

II.1/ Dry Materials

The percentage of dry materials is measured by a run through the oven at 105° C. of a sample of given initial weight until obtaining of a constant weight.

The percentage of dry materials ranges between 20 and 200 g/l, more particularly between 28 and 42 g/l.

II.2/ Measurement of the pH

The pH measured by the potentiometric method at ambient temperature leads to values ranging between 3.0 and 6.0, more particularly between 3.5 and 4.5.

II.3/ Determination of the Content of Total Sugars

The method of DUBOIS (DUBOIS M. & al [1956], Analytical chemistry, 28, No. 3 p 350-356) is used.

In the presence of concentrated sulfuric acid and phenol, the reducing sugars yield an orangey-yellow compound, From a standard range, the percentage of total sugars in a sample can be determined.

The percentage of total sugars of the active principle according to the invention is from 5 to 64 g/l, preferentially from 7 to 14 g/l.

II.4/ Characterization of the Carbohydrates a. Measuring of Simple Sugars

The percentage of simple sugars is divided into 35.3% glucose, 30.2% galacturonic acid, 15.3% arabinose, 10.1% galactose, 5.2% rhamnose, 2.8% xylose and 1.1% mannose.

b. Degree of Polymerization

The analysis of polymerization shows that the carbohydrate fraction of the active principle according to this invention is composed essentially of glucose and galacturonic acid present in the form or oligosaccharides.

| Degree of polymerization | Percentage of carbohydrates |
|---|---|
| ≦5 | 71% |
| 5 < DP < 100 | 24% |
| >200 | 5% |

II.5/ Determination of the Content of Phenolic Compounds

In the presence of potassium ferricyanide, the phenolic compounds form colored compounds, the intensity of this coloration being proportional to the quantity of phenolic compounds.

By referring to a standard range for gallic acid, in the present case from 10 to 120 mg/l, the quantity of phenolic compounds can be deduced.

The results yield 0.5 to 10.5 g/l and more particularly 0.9 to 2.3 g/l.

II.6/ Characterization of the Phenolic Compounds

The characterization and quantification of the phenolic compounds of the active principle according to this invention are accomplished by HPLC (High Performance Liquid Chromatography).

The chromatogram of the active principle according to the invention shows the presence of hydroxybenzoic compounds and flavonols, the proportions being more or less on the order of the values given in the following table:

| Phenolic compounds identified | Concentration |
|---|---|
| Flavonols | 14.5% |
| Hydroxybenzoics | 85.5% including 38% gallic acid |

III/ Evaluation of the Effect of the Active Principle Obtained According to the Invention

III.1/ Evaluation of the Effect on the Expression of the SIRT-1s

This study has as its objective to evaluate the effect of the active principle according to the invention on the expression of the SIRT-1s, proteins involved in longevity.

This study is carried out on normal human fibroblasts and senescent human fibroblasts, the aging of which is induced by successive $H_2O_2$ treatments, according to the operating protocol that follows.

On D1, the fibroblasts are sown in a complete medium, then incubated at 37° C.

On D4, the culture medium is discarded and replaced:

for the young cells,
  by culture medium for the untreated reference,
  by culture medium containing the active principle according to the invention at 0.25%, 0.5% and 1%, for the senescent cells,
  by culture medium containing $H_2O_2$ at 60 μM, in order to induce senescence, for the untreated reference,
  by medium containing $H_2O_2$ at 60 μM, in order to induce senescence, and the active principle according to the invention at 0.25%, 0.5% and 1%.

The cells then are incubated at 37° C.

On D5, D6 and D7, the cells are treated in the same manner as on D4.

On D8, the cellular extracts are recovered by potterization of the cells, then stored at −80° C. awaiting introduction of the SIRT-1s.

Introduction of the SIRT-1s is performed by Western Blot. The results, given in percentage of expression of SIRT-1 in relation to the untreated reference on normal human fibroblasts, are presented in the following table:

| | Expression of the SIRT-1s (%) | |
|---|---|---|
| | Normal human fibroblasts | Senescent human fibroblasts |
| Reference (untreated) | 100 | 77 |
| Active principle according to the invention at 0.25% | 102 | 88 |
| Active principle according to the invention at 0.5% | 111 | 97 |
| Active principle according to the invention at 1% | 136 | 108 |

It is noted that the expression of the SIRT-1s by the senescent fibroblasts is reduced significantly by 23% in relation to the normal human fibroblasts.

The active principle according to the invention introduced at 1% significantly increases the expression of the SIRT-1s by the normal fibroblasts by 36% and significantly restores the expression of the SIRT-1s by the senescent fibroblasts.

III.2/ Evaluation of the Effect on the Expression of Caveolins-1

The objective of the study is to evaluate the effect of the active principle obtained according to the invention on the expression of caveolins-1, proteins involved in cellular signaling.

This study is carried out on senescent human fibroblasts, the aging of which is induced by successive $H_2O_2$ treatments in comparison with normal human fibroblasts.

The operating protocol is the following:

On D1, the fibroblasts are sown in a complete medium, then incubated at 37° C.

On D4, the culture medium is discarded and replaced:
for the young cells, by culture medium for the untreated reference,
for the senescent cells,
by culture medium containing $H_2O_2$ at 60 μM, in order to induce senescence, for the untreated reference,
by medium containing $H_2O_2$ at 60 μM, in order to induce senescence, and the active principle according to the invention at 0.25%, 0.5% and 1%.

The cells then are incubated at 37° C.

On D5, D6 and D7, the cells are treated in the same manner as on D4.

On D8, the cellular extracts are recovered by potterization of the cells, then stored at −80° C. awaiting the introduction of the caveolins-1.

Introduction of the caveolins-1 is performed by Western Blot. The results, given in percentage of expression of caveolins-1 in relation to the untreated reference on normal human fibroblasts are presented in the following table:

|  | Expression of the caveolins-1 (%) |
| --- | --- |
| Untreated reference (normal fibroblasts) | 100 |
| Untreated reference (senescent fibroblasts) | 150 |
| Active principle according to the invention at 0.25% | 119 |
| Active principle according to the invention at 0.5% | 106 |
| Active principle according to the invention at 1% | 94 |

It is noted that the expression of the caveolins-1 by the senescent fibroblasts is increased significantly by 50% in relation to the normal human fibroblasts.

The active principle according to the invention introduced at 1% returns the expression of the caveolins-1 by the senescent fibroblasts to normal.

III.3/ Evaluation of the Effect on the Glycation of Collagen

This study has as its objective to evaluate the capacity of the active principle according to the invention to limit the glycation reaction of collagen.

The study is carried out according to the operating protocol that follows.

On D0, samples to be tested are prepared in sterile hemolysis tubes:
a non-glycated collagen reference, containing
1 ml of 3 mg/ml rat-tail collagen,
a glycated collagen reference, containing
1 ml of 3 mg/ml rat-tail collagen, and
0.3 ml of a glycoaldehyde solution at 143 mM, inducing the glycation reaction,
a positive reference, containing
1 ml of 3 mg/ml of rat-tail collagen,
0.3 ml of a solution of glycoaldehyde at 143 mM, inducing the glycation reaction, and
32 μl of aminoguanidine at 3.39 M, inhibiting the glycation reaction.
product tests, containing
1 ml of 3 mg/ml rat-tail collagen,
0.3 ml of a solution of glycoaldehyde at 143 mM, inducing the glycation reaction, and
the active principle according to the invention at 1%, 2.5% and 5%.

The samples are incubated at 37° C. protected from light for 14 days.

On D14, the fluorescence emitted by the glycation products formed is measured with the aid of a spectrofluorimeter.

The results, expressed in percentage of effectiveness, are presented in the following table:

|  | Fluorescence Value | Effectiveness (%) |
| --- | --- | --- |
| Non-glycated collagen reference | 0 |  |
| Glycated collagen reference | 449 |  |
| Positive reference | 189 | −58 |
| Active principle according to the invention 1% | 376 | −16 |
| Active principle according to the invention 2.5% | 300 | −33 |
| Active principle according to the invention 5% | 268 | −40 |

It is noted that the active principle according to the invention inhibits the glycation reaction of the collagen. This effect is dose-dependent.

III.4/ Study of the Anti-Wrinkle Properties

This study has as its objective to quantify in vivo the anti-wrinkle effectiveness of the active principle according to the invention formulated at 4% in emulsion as against placebo.

It is carried out on 21 healthy female volunteers with age ranging between 43 and 69 years.

The anti-wrinkle effectiveness is measured by means of silicon impressions made on the crow's feet of the volunteers. Analysis of these impressions with the aid of a profilometer equipped with an image analyzer makes it possible to obtain three parameters: the number of wrinkles, the total wrinkled surface and the total length of the wrinkles.

The study is conducted according to the protocol below.

Between D-15 and D0, the volunteers apply a placebo cream twice a day.

On D0, two symmetrical cutaneous zones are selected on the crow's feet, one intended to be treated with the placebo, the other with the active principle, and impressions are taken on these two zones.

Between D0 and D27, the active principle and the placebo are applied twice a day.

On D28, impressions are taken on the two zones studied.

Between D28 and D55, the active principle and the placebo are applied twice a day.

On D56, impressions are taken on the two zones studied.

The results obtained for the active principle in relation to those obtained for the placebo are expressed in percentage in the table that follows:

|  | Variation/Placebo (%) | |
| --- | --- | --- |
|  | D28 | D56 |
| Number of wrinkles | −16 | −30 |
| Total wrinkled surface | −33 | −39 |
| Total length | −25 | −36 |

It is noted that after 28 days of twice-daily applications in comparison with the placebo, the active principle obtained according to the invention formulated at 4% in emulsion at once reduces the number of wrinkles by 16%, the total wrinkled surface by 33% and the total length of the wrinkles by 25%. After 56 days, the reduction is 30% for the number of wrinkles, 39% for the total wrinkled surface and 36% for the total length of the wrinkles.

IV/ Cosmetic Composition Including the Active Principle According to the Invention This invention also covers cosmetic compositions including the active principle according to this invention in various galenical forms, in particular gel, solution, emulsion, cream . . .

It then is advisable to analyze the stability of the galenical forms including the active principle according to the invention, this in the proportions ranging between 1 and 5%.

Stability is characterized by an absence of precipitation of the active principle, an absence of creaming and an absence of phase change.

Formulations having shown a physical stability inducing 5% of the active principle according to the invention may be cited.

| | |
| --- | --- |
| Clear gel: | Carbopol: 0.5% with Triethanolamine: qsp pH = 6.5 |
| | Phenonip: 0.7% |
| | Active principle: 5.0% |
| | Water: 93.8 |
| Opaque gel: | Sepigel 305: 2.0% |
| | Phenonip: 0.7% |
| | Active principle: 5.0 |
| | Water: 92.3% |
| Emulsified gel: | Montanov 202: 3.0% |
| | Isopropyl palmitate: 12.0% |
| | Phenonip: 0.7% |
| | Sepigel 305: 2.0% |
| | Active principle: 5.0% |
| | Water: 77.3% |
| Non-ionic emulsion: | Montanov 202: 3.0% |
| | Simulsol 165: 2.0% |
| | Isopropyl palmitate: 20.0% |
| | Phenonop: 0.7% |
| | Active principle: 5.0% |
| | Water: 69.3% |
| Anionic emulsion: | Stearic acid: 7.0% |
| | Triethanolamine: 3.5% |
| | Isopropyl palmitate: 20.0% |
| | Phenonip: 0.7% |
| | Active principle: 5.0% |
| | Water: 63.8% |
| Cationic emulsion: | Quaternium-82: 5.0% |
| | Cetyl alcohol: 2.0% |
| | Isopropyl palmitate: 15.0% |
| | Cetearyl alcohol: 1% |
| | PEG 100 stearate: 1% |
| | Phenonip: 0.7% |
| | Active principle: 5.0% |
| | Water: 71.3% |

Furthermore, tests have shown the compatibility of the active principle with the raw materials used in the cosmetics industry.

The invention claimed is:

1. A method of increasing cutaneous tissue longevity and cutaneous cellular longevity, comprising applying a *Myrtus communis* active principle having:
   a percentage of dry materials ranging between 20 and 200 g/L,
   a pH ranging between 3.0 and 6.0,
   a content of total sugars ranging between 5 and 64 g/L,
   and a content of total phenols ranging between 0.5 and 10.5 g/L
   to human skin, wherein the active principle is obtained by a method comprising:
   (a) solubilizing *Myrtus communis* leaf powder in water in acid medium to form a solution,
   (b) carrying out simultaneous and/or successive enzymatic hydrolysis/hydrolyses on the solution of (a),
   (c) separating the soluble and insoluble phases of the hydrolyzed solution of (b) by filtration, centrifugation or decantation, to obtain an enzyme-containing soluble phase,
   (d) inactivating the soluble phase of (c) by thermal treatment,
   (e) purifying by clarification, thereby providing an active fraction,
   (f) concentrating the active fraction to provide a concentrated solution of the active fraction, and
   (g) filtering the concentrated solution.

2. The method according to claim 1, wherein the percentage of dry materials ranges between 28 and 42 g/l.

3. The method according to claim 1, wherein the pH ranges between 3.5 and 4.5.

4. The method according to claim 1, wherein the content of total sugars ranges between 7 and 14 g/l.

5. The method according to claim 1, wherein the content of total phenols ranges between 0.9 and 2.3 g/l.

6. The method according to claim 1, wherein the sugar content comprises glucose and/or galacturonic acid.

7. The method according to claim 1, wherein the phenol content comprises hydroxybenzoics and/or flavonols.

8. The method according to claim 1, wherein the sugar content comprises glucose and/or galacturonic acid oligosaccharides.

* * * * *